(12) United States Patent
Wang

(10) Patent No.: US 6,567,688 B1
(45) Date of Patent: May 20, 2003

(54) METHODS AND APPARATUS FOR SCANNING ELECTROMAGNETICALLY-INDUCED THERMOACOUSTIC TOMOGRAPHY

(75) Inventor: Lihong Wang, College Station, TX (US)

(73) Assignee: The Texas A&M University System, College Station, TX (US)

( * ) Notice: Subject to any disclaimer, the term of this patent is extended or adjusted under 35 U.S.C. 154(b) by 183 days.

(21) Appl. No.: 09/642,412

(22) Filed: Aug. 21, 2000

Related U.S. Application Data
(60) Provisional application No. 60/149,931, filed on Aug. 19, 1999.

(51) Int. Cl.$^7$ .................................................. A61B 5/05
(52) U.S. Cl. .................. 600/430; 600/407; 600/437; 600/438; 600/449; 600/473; 600/474; 600/477
(58) Field of Search ................................. 600/430, 407, 600/437, 438, 449, 473, 474, 477

(56) References Cited

U.S. PATENT DOCUMENTS

| | | | | |
|---|---|---|---|---|
| 4,325,257 A | * | 4/1982 | Kino et al. ................... 73/626 |
| 4,385,634 A | * | 5/1983 | Bowen ........................ 600/407 |
| 5,713,356 A | * | 2/1998 | Kruger ..................... 128/653.1 |
| 6,104,942 A | * | 8/2000 | Kruger ........................ 600/407 |
| 6,216,025 B1 | * | 4/2001 | Kruger ........................ 600/407 |
| 2002/0018510 A1 | * | 2/2002 | Murphy ........................ 374/45 |

OTHER PUBLICATIONS

L.E. Larson and J.H. Jacobi, Microwave Imaging with First Order Diffraction Tomography, *Medical Applications of Microwave Imaging* (IEEE Press, Piscataway NJ), pp. 184–212, 1986.

J.C. Lin, "Frequency optimization for microwave imaging of Biological Tissues," Proc. of IEEE 73, pp. 374–375, 1985.

S. Caorsi, A. Frattoni, G. L. Gragnani, E. Nortino, and M. Pastorino, "Numerical algorithm for dielectric–permittivity microwave imaging of inhomogeneous biological bodies," Med. & Biol. Eng. & Comput. 29, NS37–44, 1991.

M. S. Hawley, A. Broquetas, L. Jofre, J.C. Bolomey and G. Gaboriaud, "Microwave imaging of tissue blood content changes," J. Biomed Eng. 13, pp. 197–202, 1991.

P. M. Meaney, K. D. Paulsen, and J. T. Chang, "Near–Field Microwave Imaging of Biologically–Based Materials Using a Monopole Transceiver System," IEEE Trans. Microwave Theory Tech. 46, pp. 31–45, 1998.

J.C. Lin, "On Microwave–Induced Hearing Sensation," IEEE Trans. Microwave Theory and Tech. MTT25, pp. 605–613, 1977.

F. Caspers and J. Conway, "Measurement of power density in a lossy material by means of electromagnetically–induced acoustic signals for non–invasive determination of spatial thermal absorption in connection with pulsed hyperthermia," Proc. of the 12th European Microwave Conference, pp. 565–568, 1982.

(List continued on next page.)

*Primary Examiner*—Marvin M. Lateef
*Assistant Examiner*—Devaang Shah
(74) *Attorney, Agent, or Firm*—Baker Botts L.L.P.

(57) ABSTRACT

A microwave-induced thermoacoustic tomography system and method is provided to image biological tissue. Short microwave pulses irradiate tissue to generate acoustic waves by thermoelastic expansion. The microwave-induced thermoacoustic waves are detected with an ultrasonic transducer or transducer array. Each time-domain signal from the ultrasonic transducer is converted to a one-dimensional image along the acoustic axis of the ultrasonic transducer. Scanning the system perpendicularly to the acoustic axis of the ultrasonic transducer generates multi-dimensional images in real time without computational image reconstruction.

48 Claims, 13 Drawing Sheets

OTHER PUBLICATIONS

Jenn–Lung Su and J.C. Lin, "Thermoelastic Signatures of Tissue Phantom Absorption and Thermal Expansion," IEEE Trans. Biomed. Eng. 43, pp. 178–182, 1987.

J.S.K. Wan, "Microwaves and Chemistry: The Catalysis of an Exciting Marriage," Res. Chem. Intermed. 19, pp. 147–158, 1993.

T. Bowen, R. L. Nasoni, A. E. Pifer, and G. H. Sembroski, "Some Experimental Results on the Thermoacoustic Imaging of Tissue Equivalent Phantom Materials," Proc. IEEE Ultrasonics Symposium pp. 823–827, 1981.

R.G. Olsen, "Generation of Acoustic Images from the Absorption of Pulsed Microwave Energy," J P. Powers, eds., (Plenum Publishing, New York), pp. 53–59, 1982.

R. G. Olsen and J.C. Lin, "Acoustic Imaging of a Model of a Human Hand Using Pulsed Microwave Irradiation," Bioelectromagnetics 4, pp. 397–400, 1983.

J.C. Lin and K. H. Chan, "Microwave Thermoelastic Tissue Imaging—System Design," IEEE Trans. Microwave Theory and Tech. 32, pp. 854–860, 1984.

R. L. Nasoni, G. A. Evanoff, Jr., P. G. Halverson, and T. Bowen, "Thermoacoustic Emission by Deeply Penetrating Microwave Radiation," Proc. IEEE Ultrasonics Symposium 5, pp. 633–637, 1984.

K.H. Chan and J.C. Lin, "Microwave–Induced Thermoelastic Tissue Imaging," IEEE Engineering in Medicine and Biology Society 10th Annual International Conference, pp. 445–446, 1988.

R. A. Kruger, D. R. Reinecke, and G. A. Kruger, "Thermoacoustic Computed Tomography—Technical Considerations," Med. Phys., accepted, 1999.

R. A. Kruger, K. K. Kopecky, A. M. Aisen, D. R. Reinecke, G. A. Kruger, and W. L. Kiser, Jr., "Thermoacoustic CT with Radio Waves: A Medical Imaging Paradigm," Radiology 211, pp. 275–278, 1999.

R.A. Kruger and P. Liu, "Photoacoustic Ultrasound: Pulse production and detection in 0.5% Liposyn," Med. Phys. 21, pp. 1179–1184, 1994.

R.A. Kruger, P.Liu, Y. "Richard" Fang, and C.R. Appledorn, "Photoacoustic ultrasound (PAUS)—Reconstruction tomography," Med. Phys. 22, pp. 1605–1609, 1995.

A. A. Oraevsky, R. Esenaliev, F. K. Tittel, M. R. Ostermeyer, L.H. Wang, and S. L. Jacques, "Laser acoustic imaging of turpid media: determination of optical properties by comparison with diffusion theory and Monte Carlo stimulation," LaserTissue Interaction VII 2681, pp. 277–284, 1996.

C.G.A. Hoelen, F.F.M. de Mul, R. Pongers, and A. Dekker, "Three–dimensional photoacoustic imaging of blood vessels in tissue," Opt. Lett. 23, pp. 648–650, 1998.

C. Gabriel, S. Gabriel, and E. Corthout, "The dielectric properties of biological tissues: I. Literature survey," Phys. Med. Biol. 41, pp. 2231–2249, 1996.

S. Gabriel, R. W. Lau, and C. Gabriel, "The dielectric properties of biological tissues: II Measurements in the frequency range 10 Hz to 20–GHz," Phys. Med. Biol. 41, pp. 2251–2269, 1996.

S. Gabriel, R. W. Lau, and C. Gabriel, "The dielectric properties of biological tissues: III Parametric models for the dielectric spectrum of tissues," Phys. Med. Biol. 41, 2 pp. 2271–2293, 1996.

F. A. Duck, Chapter 2, "Thermal Properties of Tissue"; pp. 9–42; Chapter 4, "Acoustic Properties of Tissue at Ultrasonic Frequencies," pp. 73–135; and Chapter 7, "Ionising Radiation and Tissue," pp. 225–277, *Physical Properties of Tissue: a Comprehensive Reference Book* (Academic Press, London, New York), 1990.

L.H. Wang, X. Zhao, H. Sun, and G. Ku, "Microwave–induced acoustic imaging of biological tissues," Rev. Sci. Instrum., in press, 1999.

G. J. Diebold, and T. Sun, "Properties of Photoacoustic Waves in One, Two and Three Dimensions," Acoustica, 80, pp. 339–351, 1994.

C.G.A. Hoelen, F.F.M. de Mul, and J. Greve, "Non–destructive photoacoustic subsurface tissue imaging: a feasibility study," Proc. SPIE pp. 26–28, 1995.

A.O. Oraevsky, S.L. Jacques, and F.K. Tittel, "Measurement of tissue optical properties by time–resolved detection of laser–induced transient stress," Appl. Opt. 36, pp. 402–415, 1997.

* cited by examiner

METHODS AND APPARATUS FOR SCANNING ELECTROMAGNETICALLY-INDUCED THERMOACOUSTIC TOMOGRAPHY

REFERENCE TO PRIOR APPLICATION

The present application is based on U.S. Provisional Patent Application Serial No. 60/149,931, filed Aug. 19, 1999.

FIELD OF THE INVENTION

The present invention relates to electromagnetically-induced thermoacoustic imaging and, more specifically, to real-time scanning electromagnetically-induced thermoacoustic imaging of biological tissues.

BACKGROUND OF THE INVENTION

Electromagnetically-induced thermoacoustic imaging is based on the photoacoustic effect, i.e., the generation of acoustic waves by the deposition of short-pulse electromagnetic energy safely into biological tissues. The electromagnetic wave (microwave or radio frequency) for this technology is short-pulsed, and its power is within the IEEE safety limits. The electromagnetically-induced acoustic wave is detected with an ultrasonic detector or detector array for imaging. The contrast between tumors and normal tissues in the microwave regime is very good. Cancerous breast tissues, for example, are found to be 2–5 times more strongly absorbing than surrounding normal breast tissues in the microwave range, which has been attributed to an increase in bound water and sodium within malignant cells.

Purely-microwave imaging of biological tissues, however, is fundamentally limited to poor resolution (on the order of 10 mm) because of the larger wavelength of microwave. Also, purely-microwave imaging has had difficulties in multi-channel detection of microwave without cross coupling, in reconstruction algorithms, and especially in achieving good spatial resolution because of the strong diffraction of microwaves. Purely-ultrasound imaging (ultrasonography), an established medical imaging modality, can yield good spatial resolution, but has poor contrast for early-stage tumors. Electromagnetically-induced thermoacoustic imaging, and microwave-induced thermoacoustic imaging in particular, can potentially bridge the gap and fuse the advantages of the two imaging modalities.

If optical radiation instead of microwave radiation is used, this thermoacoustic phenomenon is better known as photoacoustics. Microwave-induced thermoacoustic imaging shares similar principles with its optical counterpart. However, microwave-induced thermoacoustic imaging may find unique applications in medical imaging because microwave radiation provides a deeper penetration depth in biological tissues than light and has different contrast mechanisms.

Microwave-induced thermoacoustics has been used to quantify physical parameters in media such as the power density and the concentration of a given substance. Several investigators have employed microwave-induced thermoacoustics in the 1980s for imaging of biological tissues. These early works, however, did not produce any tomographic or depth-resolved images. Recently, images of biological tissues have been computationally reconstructed based on microwave-induced thermoacoustics. This approach requires the measurement of a large amount of data around the tissue and post-processing computation.

X-ray mammography is the current standard clinical tool for breast cancer screening. Although effective, it has difficulties in imaging premenopausal breasts, and has the medical and environmental disadvantages attendant upon the use of ionizing radiation.

SUMMARY OF THE INVENTION

In accordance with the invention, methods and apparatus for real-time, non-invasive electromagnetically-induced thermoacoustic scanning of biological tissue are provided, in which the tissue to be imaged is irradiated with short pulses of electromagnetic energy and the resulting induced thermoacoustic waves are detected by one or more ultrasonic transducers to provide a time-domain signal. The time-domain signal is converted to a spatial one-dimensional image of the tissue along the transducer axis. By utilizing a one-dimensional array of transducer elements or by scanning the tissue in a direction transverse to the transducer axis and repeating the irradiating, detecting and signal-converting steps at spaced points along the transverse direction, a two-dimensional image of the tissue is provided. A three-dimensional image may be provided by repeating the foregoing steps in a second direction transverse to both the transducer axis and the first direction. In accordance with the invention, such two-dimensional and three-dimensional images are provided in real time without computational reconstruction of the image.

The applied electromagnetic energy field is preferably compressed to a narrow wave to minimize the exposed volume of tissue and to improve image quality. A tapered waveguide may be employed for that purpose. The acoustic axis of the focused ultrasonic transducer or of the transducer array, is located in the volume of the electromagnetic wave. A curved illumination interface may be provided between the waveguide and the tissue to enhance efficient energy transfer to the tissue and to focus the electromagnetic energy within the region of the tissue to be imaged. This may be accomplished by curving the tissue itself, or by curving the exit end of the waveguide and bending the tissue surface accordingly.

In an advantageous embodiment of the invention, the electromagnetic energy is in the microwave range and preferably within the range of from 300 MHz to 3 GHz. The microwave pulse width is preferably within the range of from 0.1 $\mu$s to 0.5 $\mu$s.

The ultrasonic transducer may comprise a single-element focused transducer or multiple single-element focused transducers forming an array. Alternatively, an array of unfocused transducers may be used, in which case synthetic focusing of the output signals is employed to generate the two-dimensional tomographic images.

For better visualization of deeper tissues, the transducer signals may be gain compensated to offset electromagnetic wave attenuation within the tissue.

The electromagnetically-induced thermoacoustic scanning technique of the invention is compatible with existing ultrasonographic equipment. In accordance with the invention, both thermoacoustic images and ultrasonograms may be recorded of the same sampling cross section or volume, thereby providing both types of images in real time for co-registration. The diagnostic information available to the physician is thus enhanced.

The advantages of the invention relative to prior imaging technologies include the use of non-ionizing radiation, enhanced imaging resolution, increased penetration depth, high contrast between tumors and normal tissues, real-time imaging, and co-registration between thermoacoustic images and ultrasonographic images.

BRIEF DESCRIPTION OF THE DRAWINGS

For a more complete understanding of the present invention and the advantages thereof, reference is now made to the following description taken in conjunction with the accompanying drawings, wherein like reference numerals represent like parts, in which.

DETAILED DESCRIPTION OF EXEMPLARY EMBODIMENTS

Microwave-induced thermoacoustic imaging is based on the detection of the thermoacoustic signals generated by microwaves in the sample tissues. Pulsed microwave radiation is used to irradiate the samples. Absorbed microwave energy causes thermoelastic expansion that radiates acoustic waves. An ultrasonic transducer detects the time-resolved thermoacoustic signals.

The electric field strength of a plane wave in a lossy media is attenuated exponentially as $$E = E_0 \exp(-\alpha z), \quad (1)$$

where $E_0$ is the electrical field at the sample surface, E is the electrical field at the depth z, and $\alpha$ is the electric-field absorption coefficient expressed as $$\alpha = \omega \sqrt{\frac{\mu \varepsilon}{2} \left[ \sqrt{1 + \left(\frac{\sigma}{\omega \varepsilon}\right)^2} - 1 \right]}, \quad (2)$$

where $\omega$ is the angular frequency, $\mu$ is the permeability, $\in$ is the permittivity, and $\sigma$ is the conductivity. The induced thermoacoustic pressure depends on the microwave intensity and the complex dielectric constant of the material. In the frequency range of 0.1–10-GHz, the dielectric constant (ratio of the permittivity in material to that in vacuum) has a value of 5–70 for soft tissues, and the conductivity has a value of 0.02–3 S/m. The dielectric properties of tissues determine the absorption of microwave at various microwave frequencies.

Water and ion concentrations are key factors in microwave absorption. Muscle and fat tissues respectively have very high and very low water contents and therefore have the extreme microwave absorption properties. Most other soft tissues have an absorption coefficient in between those for muscle and fat tissues. This wide range of values among various tissues is desired for a high imaging contrast. Importantly for breast cancer screening, malignant breast tissues are more strongly absorbing than surrounding normal breast tissues.

Figure 1:
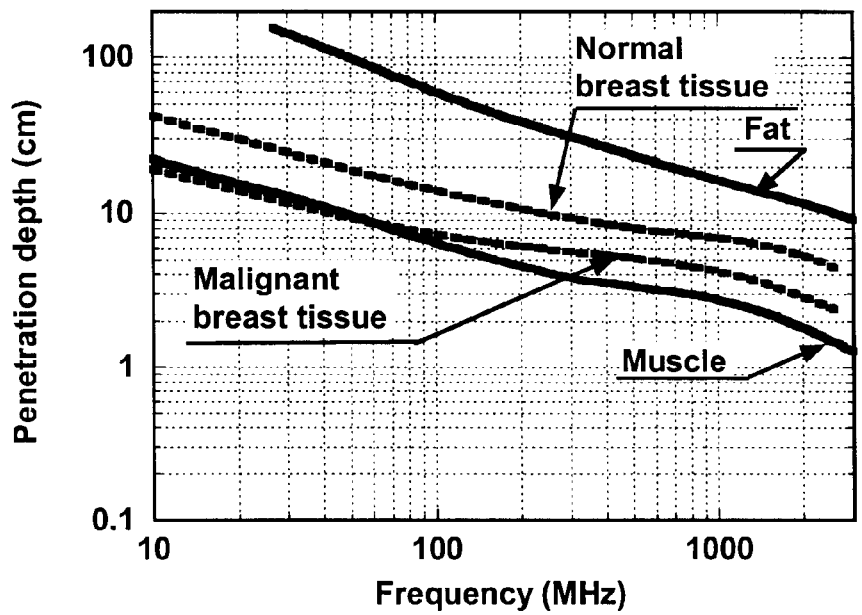
FIG. 1 is a graphical representation of the penetration of radiowave and microwave radiation in human fat, muscle and breast tissue.

FIG. 1 shows the penetration depth of electromagnetic waves in human tissues as a function of the electromagnetic frequency in the radio frequency (RF) region, where the penetration depth is the inverse of the absorption coefficient. The penetration depths of muscle and fat tissues are plotted in solid lines. C. C. Johnson et al., "Non-ionizing Electromagnetic Wave Effects in Biological and System," Proc. IEEE, 60, 692–718 (1972).

As shown in FIG. 1, at 3 GHz the penetration depths for fat and muscle are 9 cm and 1.2 cm, respectively, while at 500 MHz, the penetration depths for fat and muscle are 23.5 cm, and 3.4 cm, respectively. This wide range of values among various tissues can provide a high imaging contrast for biological tissues.

The penetration depths of normal and malignant human breast tissues are plotted in FIG. 1 in dashed lines. At 3 GHz, the penetration depths for malignant and normal breast tissue are approximately 2.3 cm and 4.4 cm, respectively. It may be seen, therefore, that microwave-induced thermoacoustic imaging may potentially be used to detect early-stage cancers.

Figure 2:
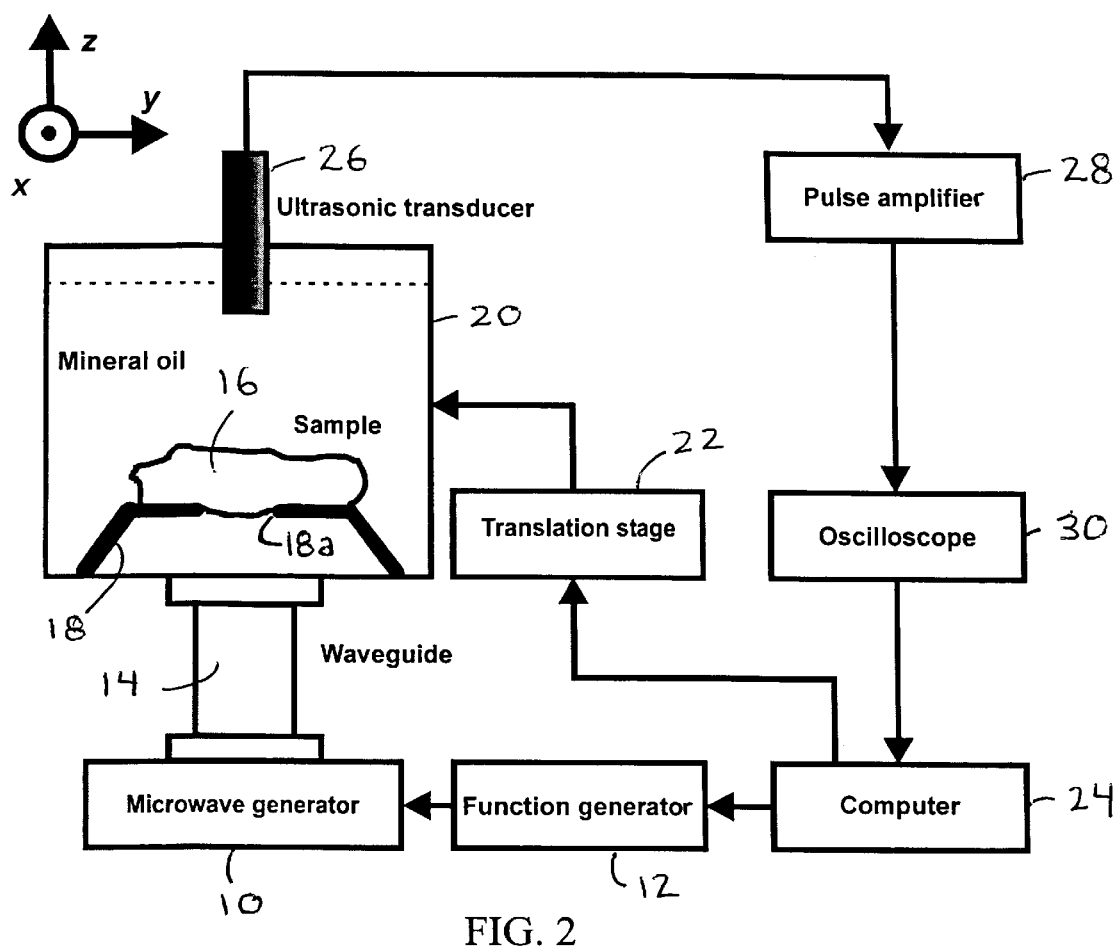
FIG. 2 is a schematic diagram illustrating a scanning thermoacoustic tomography system in accordance with one embodiment of the present invention.

A system for scanning thermoacoustic tomography in accordance with an embodiment of the present invention is shown in FIG. 2. A Cartesian coordinate system is set up for reference. The z axis is along the acoustic axis pointing upward. The x axis is perpendicular to the drawing plane and points outward. The y axis is in the drawing plane pointing to the right. A microwave generator 10 transmits microwave pulses at a maximum peak power of approximately 30 kW. The frequency of the microwave energy should be selected based upon the required imaging depth for a specific problem. See FIG. 1. A higher frequency may be selected for imaging thin tissues, and vice versa. In the embodiment of FIG. 1, the microwave frequency is preferably within the range of 300 MHz to 3 GHz, and the pulse width is preferably within the range of 0.1 $\mu$s to 0.5 $\mu$s. Unless otherwise stated, the exemplary embodiment described below has a frequency of 3 GHz and a pulse width of 0.5 $\mu$s.

A function generator 12 (DS345, Stanford Research System) is employed to trigger the microwave generator 10, control its pulse repetition frequency, and synchronize the oscilloscope sampling. Microwave energy is delivered by a rectangular waveguide 14 with a cross section of 72 mm×34 mm. The sample 16 to be imaged is placed on a plastic stand or holder 18 inside a plexiglass container 20 filled with mineral oil. The container 20 is fixed on a two-dimensional x-y translation stage 22 (MD2, Arrick Robotics). A personal computer 24 controls the two stepper motors to drive the translation stage 22 in the x and y directions. Both mineral oil and plexiglass have a small absorption coefficient for microwaves. Mineral oil also provides good acoustic coupling. An ultrasonic transducer 26 is immersed in the mineral oil facing the microwave waveguide 14. The holder 18 preferably has an opening 18a aligned with the acoustic axis of the transducer 26 to minimize interference with the microwave propagation. The transducer 26 is connected to a pulse amplifier 28 of a 25-MHz bandwidth. The amplified signal is recorded and averaged 10–100 times by an oscilloscope (TDS640A, Tektronix) and then transferred to the personal computer 24 for data conversion and imaging as discussed below.

The ultrasonic transducer (V314, Panametrics) may have a central frequency of 1 MHz with a bandwidth of 0.6 MHz, a diameter of 1.9 cm, and a focal length at 1 MHz of 2.5 cm. Alternatively, the ultrasonic transducer (V384, Panametrics) may have a central frequency of 3.5 MHz, a bandwidth of 2.5 MHz, a diameter of 0.64 cm, and a focal length at 3.5 MHz of 1.8 cm. Unless otherwise stated, the 1 MHz ultrasonic transducer was used to obtained the results discussed below.

Because the propagation speed of electromagnetic waves is much greater than the speed of sound, the microwave pulses stimulate the entire tissue sample essentially simultaneously. The induced thermoacoustic waves take different travel times to reach the ultrasonic transducer 26.

The ultrasonic transducer 26 measures the time-of-arrival signals of the thermoacoustic waves. The distance between the thermoacoustic source within the sample 16 and the transducer is calculated by multiplying the time of arrival with the speed of sound in the medium. Therefore, a time-domain signal is converted into a one-dimensional image along the acoustic axis (z axis), which is similar to an ultrasonic A-scan image. Scanning the sample along the x or y axis and combining the multiple one-dimensional images yields a two-dimensional cross sectional image of the sample in the x-z or y-z plane. Scanning along both the x and y axes yields a three-dimensional image.

Although scanning is accomplished in the embodiment of FIG. 2 by translating the sample relative to the transducer, it will be understood that the same effect can be achieved by translating the ultrasonic transducer relative to the sample. Indeed, in the case of breast cancer screening or other in vivo human or animal imaging, it would normally be preferable to translate the transducer relative to the tissue region being imaged. As used herein, therefore, the term "scanning" is intended to encompass both translation of the sample tissue and translation of the transducer.

A single-element focused transducer is shown in FIG. 2. Besides the use of a single-element focused ultrasonic transducer, two other alternatives exist to increase the data acquisition speed and potentially the imaging quality as well. The first alternative is to use multiple single-element focused ultrasonic transducers, forming an array. All the transducers will receive the thermoacoustic signals simultaneously upon emission of each electromagnetic pulse. Each signal is then converted to a one-dimensional image along the corresponding acoustic axis. This alternative will produce the same image that a single-element focused ultrasonic transducer would by scanning it along the direction of the array.

The second alternative is to use multiple single-element unfocused ultrasonic transducers, forming an array. Again, all the transducers will receive thermoacoustic signals simultaneously upon emission of each electromagnetic pulse. Synthetic focusing in the computer 24 would then be employed to convert the multi-channel data into a two-dimensional image of the cross section under the array. With the same multi-channel data set, synthetic focusing can be directed to various focal spots along both of the dimensions under the array. This type of array provides improved imaging quality compared with focused transducers that have a fixed focal length, where the focal spot in tissue cannot be varied along the acoustic axis unless the transducers are scanned along the acoustic axis. Synthetic focusing, also called synthetic aperture, is a well established technique, and hence is not detailed here. Where the ultrasonic transducer is translated, its acoustic axis remains within the volume of the electromagnetic wave through the full range of translation. In practice, this volume is sufficient to allow movement of the transducer over the tissue region to be scanned.

Of course, the arrays in both of the alternatives can be made two dimensional to obtain three-dimensional volumetric images simultaneously. When the costs of two-dimensional arrays become competitive, their use for this invention would be attractive. In this case, the irradiated volume by the electromagnetic wave should cover the entire imaging volume.

The generation of thermoacoustic waves by deposition of microwave energy can be described by the following differential equation:

$$\left(\nabla^2 - \frac{1}{v_s^2}\frac{\partial^2}{\partial t^2}\right)p(r,t) = -\frac{\beta}{C_p}\frac{\partial H}{\partial t}, \quad (3)$$

where p(r,t) is the thermoacoustic pressure at the position r and time t, $v_s$ is the speed of sound, $\beta$ is the isobaric volume expansion coefficient, $C_p$ is the heat capacity, and H is the heating function describing the microwave-energy deposition in the sample per unit volume per unit time. Thermal-confinement condition is assumed, where the acoustic transit time across the acoustic source is less than the heat conduction time. The solution of the three-dimensional wave equation under the zero-initial-value conditions p(0,r)=0 and $$\frac{\partial}{\partial t}p(0,r) = 0$$

can be expressed as an integral:

$$p(r,t) = \frac{\beta}{4\pi C_p}\int\int\int \frac{1}{|r-r'|}\frac{\partial H(r',t')}{\partial t'}dr'. \quad (4)$$

The integral is calculated inside a sphere with a radius of $v_s t$ centered at r, and r' is the space inside the sphere where microwave is absorbed and acoustic signal is generated. In the integration, the heating function is not taken at time t but at an earlier time $t'=t-|r-r'|/v_s$; therefore, the integration function is also called retarded potential. Analytic solutions can be obtained for simple geometric structures such as an infinite layer, a sphere, and a cylinder under delta heating, where the heating function is a delta function in time.

Figure 3:
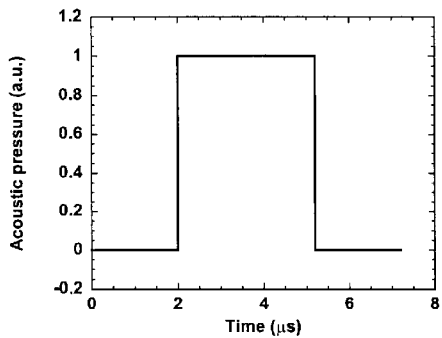
FIGS. 3(a)–3(e) are graphic illustrations of simulations of the ultrasonic transducer (piezo-electric) signals in response to the microwave-induced thermoacoustic signals from a 4.8-mm thick gel slab, and more specifically, (a) thermoacoustic signal in a slab induced by an ideal microwave impulse; (b) temporal profile of the microwave pulses used in the experiment; (c) thermoacoustic signal in a slab induced by the microwave pulses used in the experiment; (d) piezo-electric impulse response of the ultrasonic transducer; and (e) experimental and simulated piezo-electric outputs of the ultrasonic transducer in response to the thermoacoustic signals.
Figure 3:
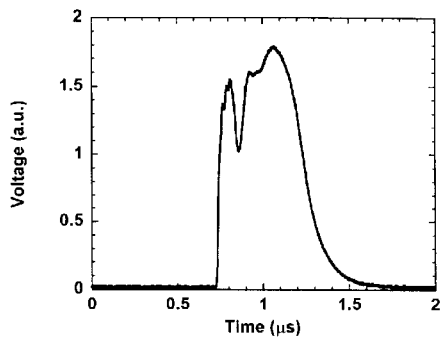
Figure 3:
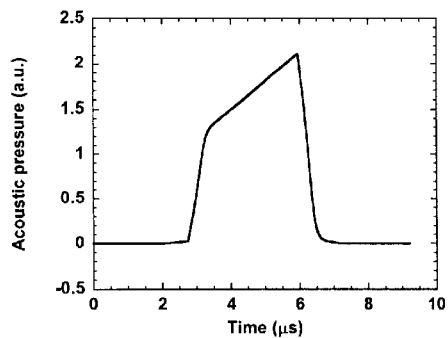
Figure 3:
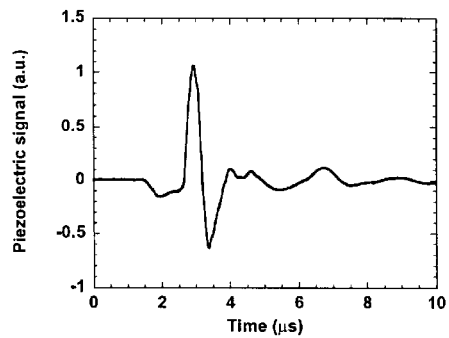
Figure 3:
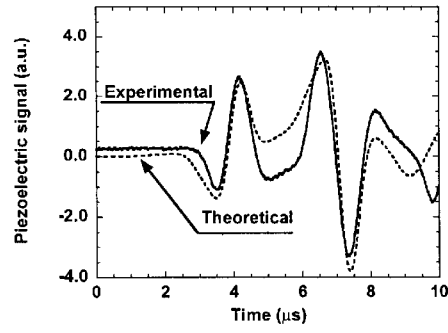

For a slab with a thickness d under delta heating, the impulse-response pressure is $$p_1(z,t) = \frac{\beta v_s^2}{2C_p}u(z - v_s t) \quad (5)$$

where $u(z-v_s t)$ is defined as a function that is unity when $0 \leq (z-v_s t) \leq d$ and zero otherwise. The impulse response is a traveling square wave as shown in FIG. 3(a) for a 4.8-mm gel slab if the microwave attenuation across the slab is negligible. Because, as noted, the propagation speed of electromagnetic wave is much greater than the speed of sound, the sample volume illuminated by microwave pulses radiates acoustic waves simultaneously.

The heating function in one-dimensional lossy media may be expressed as $H(z,t)=\alpha e^{-\alpha z}s(t)$, where $\alpha$ is the microwave absorption coefficient, and s(t) is the temporal profile of the microwave pulse. FIG. 3(b) shows the temporal profile of the microwave pulses.

The thermoacoustic pressure induced by the microwave pulses can be derived by the following convolution:

$$p(z,t) = \int p_1(z,\tau)H(z,t-\tau)d\tau \quad (6)$$

FIG. 3(c) illustrates the thermoacoustic pressure at the ultrasonic transducer generated from the slab, which is obtained by convolving the two temporal waveforms in FIGS. 3(a) and 3(b) by use of Eq. (6).

For more general non-thermal-confined cases when heat transfer in the medium cannot be neglected, the following heat conduction equation must be taken into account in the pressure calculation:

$$\rho C_p \frac{\partial T(r,t)}{\partial t} = k\nabla^2 T(r,t) + H(r,t), \quad (7)$$

where $\rho$ is the density of the medium, k is the thermal conductivity, and T(r,t) is the temperature distribution in the microwave-illuminated space. The thermoacoustic pressure is:

$$p(r,t) = \frac{\beta}{4\pi C_p}\int\int\int \frac{1}{|r-r'|}\left[\frac{\partial H(r',t')}{\partial t'} + k\nabla^2\frac{\partial T(r',t)}{\partial t'}\right]dr'. \quad (8)$$

The integration involves the heat conducted from the surrounding medium besides the heat due to the absorbed microwave energy.

The piezo-electric impulse response q(t) of the ultrasonic transducer is shown in FIG. 3(d). The piezo-electric output of the ultrasonic transducer in response to thermoacoustic pressure can be calculated by the following convolution between the thermoacoustic pressure at the transducer and the impulse response of the transducer:

$$P_0(z,t) = \int p(z,\tau)q(\tau-t)d\tau \quad (9)$$

The piezo-electric signal from a 4.8-mm slab is obtained by the convolution of the two waveforms in FIGS. 3(c) and 3(d) with Eq. (9) and is plotted in FIG. 3(e) as a dashed line.

The piezo-electric signal from a 4.8-mm gel slab is plotted in FIG. 3(e) as a solid line for comparison, where the slight DC offset is caused by the DC drift of the amplifier in the experimental detection. There are two dipoles in each waveform in FIG. 3(e), and the signal between the dipoles is weak. The polarity, the width of each dipole, and the distance between the two dipoles are in good agreement between the theory and experiment. Because the piezo-electric signal of the ultrasonic transducer can be simulated by the two convolutions as shown above, the dipole width is related to the width of the microwave pulses and the width of the impulse response of the ultrasonic transducer, which were 0.5 $\mu$s and 1.7 $\mu$s, respectively. The time intervals between the zero-crossing points of the two dipoles in the two waveforms are determined by the slab thickness and are equal to the acoustic transit time 3.2 $\mu$s over the 4.8-mm-thick slab.

Dipoles are also observed in photoacoustics by lasers, where a Q-switched laser with a pulse width of ~10 ns and a wideband ultrasonic transducer are employed. The detected dipoles of FIG. 3(e) resemble the well-known dipoles that originate from small spherical or cylindrical objects excited by laser pulses or from acoustic reflection at soft acoustic interfaces. However, the detected dipoles in the thermoacoustic signals in slabs resulted from the limited bandwidth of the ultrasonic transducers.

Figure 4:
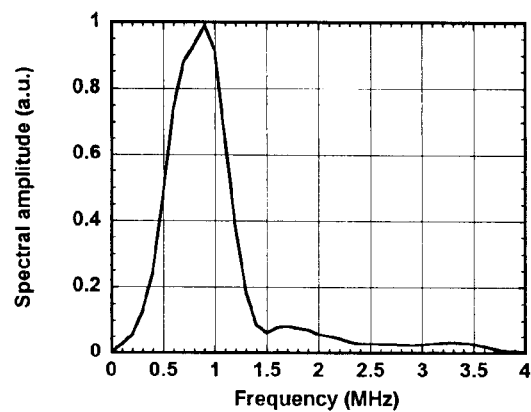
FIGS. 4(a)–4(c) are graphic illustrations of frequency-domain analysis of the microwave-induced thermoacoustic signals; and more specifically, (a) spectrum of a 1-MHz ultrasonic transducer; (b) spectrum of the microwave-induced thermoacoustic signal; and (c) spectrum of the piezo-electric signal, which is the filtered microwave-induced thermoacoustic signal.
Figure 4:
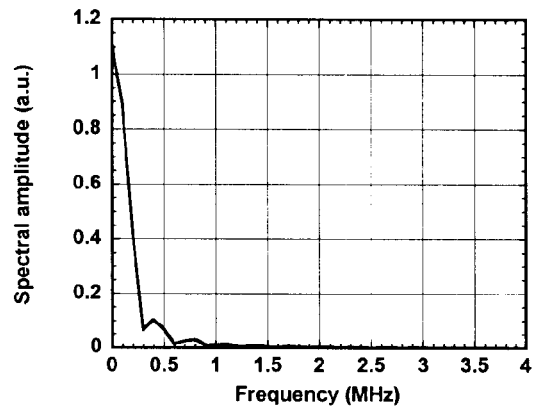
Figure 4:
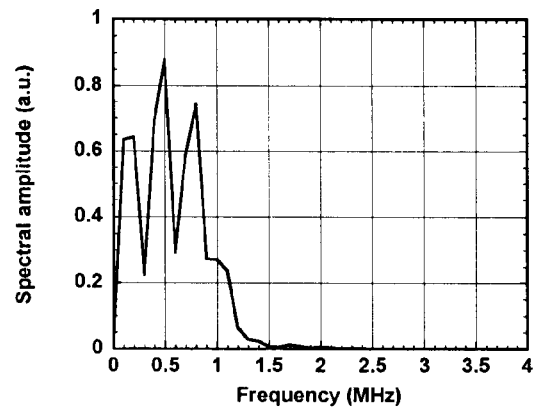

This phenomenon can also be explained in the frequency domain, where the ultrasonic transducer acts as a bandpass filter. A frequency spectrum of the ultrasonic transducer is shown in FIG. 4(a). The temporal profile of the thermoacoustic pressure varies sharply near the slab boundaries and slowly inside the slab as shown in FIG. 3(c). The corresponding spectrum is peaked at DC as shown in FIG. 4(b). The filtered spectrum is peaked near 0.5 MHz as shown in FIG. 4(c), where the DC is rejected and the low-frequency components are attenuated significantly. In other words, the ultrasonic transducer cannot respond efficiently to the thermoacoustic waves emitted between the sample boundaries, which have a lower-frequency spectrum. Therefore, the observed piezo-electric signal between the two sample boundaries is low.

Figure 5:
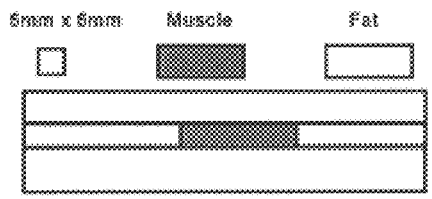
FIGS. 5(a)–5(c) are graphical illustrations of (a) cross section of a fat-muscle-fat sample on the y-z plane; (b) two-dimensional image of the y-z cross section of the sample obtained by scanning thermoacoustic tomography; and (c) temporal microwave-induced thermoacoustic signal along the vertical center line of the sample, in which a 1-MHz ultrasonic transducer was used.
Figure 5:
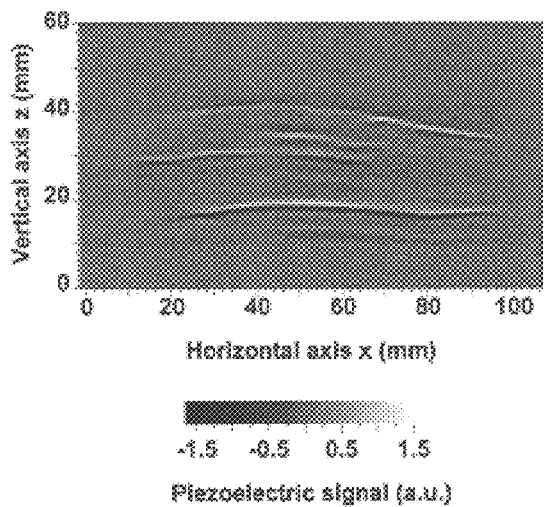
Figure 5:
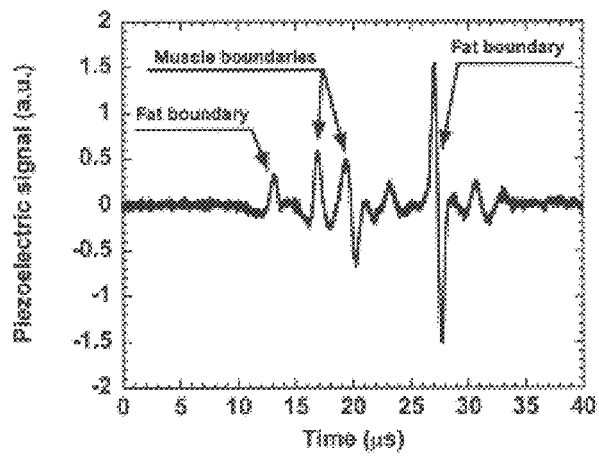

A tissue sample with a fat-muscle-fat structure as shown in FIG. 5(a) is placed on the plastic stand 18 inside the container 20 as shown in FIG. 2. FIG. 5(b) shows a 2D image of the sample obtained with the scanning thermoacoustic tomography technique of the present invention. Thermoacoustic signals are acquired in the time domain while the fat-muscle-fat sample is scanned horizontally along the y axis with a step size of 1 mm. The 2D image of the sample is formed by combining these temporal waveforms taken successively at the scanning stops along the y axis. Each vertical line in this 2D image is from a temporal waveform. The muscle inside the fat is clearly visible with a good contrast. The fat-tissue interface to the left of the muscle is also visible, which is possibly caused by the slight difference in the microwave properties between the two fat sections.

FIG. 5(c) illustrates a time-domain waveform measured above the center of the sample at y equal to 54 mm. The strongest dipole near 27 $\mu$s is from the bottom boundary of the sample where microwave experienced the least attenuation, whereas the weakest dipole near 14 $\mu$s is from the top boundary of the sample where microwave experienced the most attenuation. The two dipoles corresponding to the boundaries of the muscle layer are also clearly distinguishable. The time intervals between the adjacent dipoles agree with the thickness values of the tissue layers very well. However, the vertical boundaries of the muscle slab are not visible in the image because the thermoacoustic waves from these boundaries propagate perpendicularly to the acoustic axis of the ultrasonic transducer and therefore cannot be received by the transducer.

The axial resolution along the acoustic axis (z axis) is determined by the width of the thermoacoustic dipoles, which is related to the width of the microwave pulse and the width of the impulse response of the transducer (the inverse of the bandwidth of the ultrasonic detector). The bandwidth of the ultrasonic transducer should be selected to cover the bandwidth of the thermoacoustic signal as much as possible. With a 1-MHz ultrasonic transducer, the width of the thermoacoustic signal is estimated to be 2.2 $\mu$s, which is the sum of the width of the microwave pulses (0.5 $\mu$s) and the width of the impulse response of the transducer (1.7 $\mu$s). Because the speed of sound in tissue is 1.5 mm/$\mu$s, the corresponding axial resolution should be approximately 3.3 mm along the z axis. For a 3.5-MHz ultrasonic transducer, the axial resolution is improved to approximately 1.4 mm.

Figure 6:
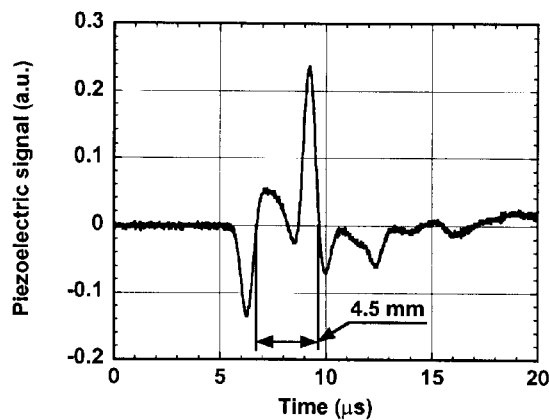
FIGS. 6(a)–6(c) are scanned microwave-induced thermoacoustic signals in gel slabs of various thickness values: (a) 4.5 mm, (b) 3.8 mm, and (c) 2 mm, in which a 1-MHz ultrasonic transducer was used.
Figure 6:
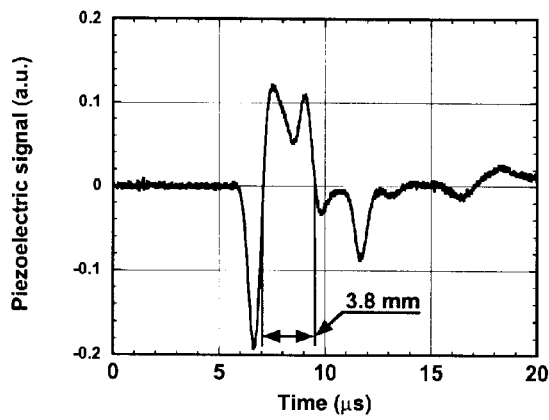
Figure 6:
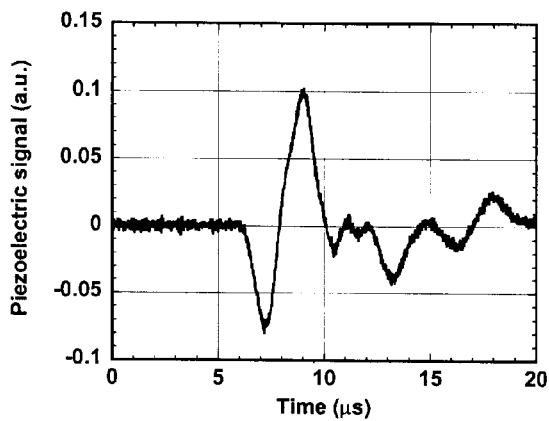

FIGS. 6(a)–6(c) show the thermoacoustic signals from slab samples of various thickness values measured by a 1-MHz ultrasonic transducer. The slab samples are made of 5% gelatin and 5% NaCl, where NaCl controlled the microwave absorption. As the thickness of the samples decrease, the temporal distance between the adjacent dipoles corresponding to the two boundaries of the slabs decreases as well. The two dipoles became barely distinguishable when the thickness is reduced to 3.8 mm, and completely inseparable when the thickness is reduced to 2 mm. Therefore, the measured axial resolution is ~3.8 mm, close to the above calculated resolution of 3.3 mm based on the dipole width. The discrepancy is caused by the long tail of the dipoles. The relative variation in intensity between the two dipoles is caused by microwave attenuation in the slabs.

Figure 7:
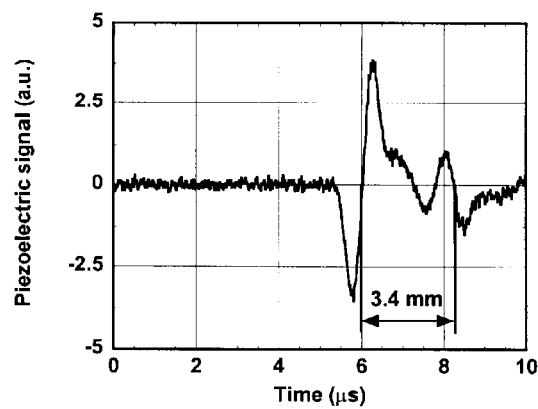
FIGS. 7(a)–7(c) are scanned microwave-induced thermoacoustic signals in gel slabs of various thickness values: (a) 3.4 mm, (b) 1.9 mm, and (c) 1 mm, in which a 3.5-MHz ultrasonic transducer was used.
Figure 7:
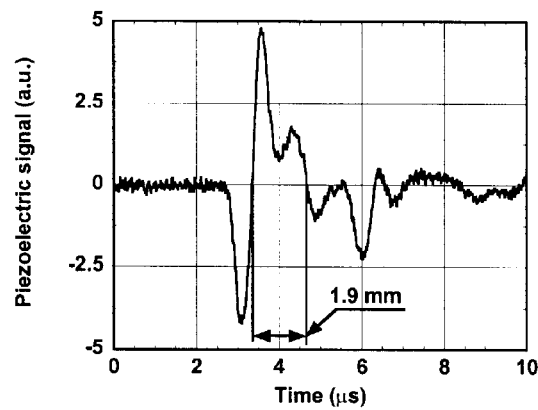
Figure 7:
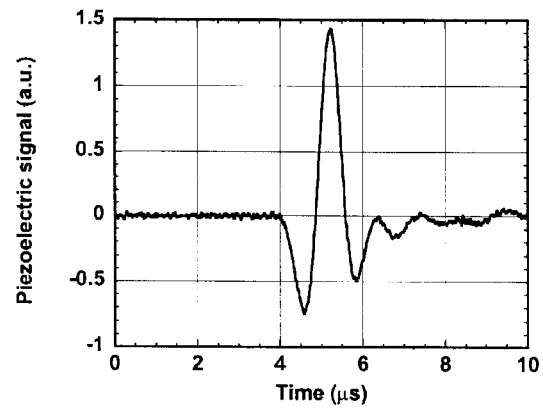

Similarly, FIGS. 7(a)–7(c) show the thermoacoustic signals from slab samples of various thickness values measured by a 3.5-MHz ultrasonic transducer. The measured axial resolution is ~1.9 mm, close to the above calculated resolution of 1.4 mm based on the dipole width. As expected from the theoretical consideration, the wider-bandwidth transducer produced better axial resolution. Potentially, shorter microwave pulses and deconvolution may be used to improve the axial resolution further.

Figure 8:
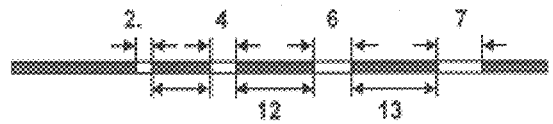
FIGS. 8(a)–8(c) are scanned two-dimensional tomographic images of a linear array of gel slabs obtained by scanning thermoacoustic tomography: (a) y-z cross section of the sample (units in mm); (b) image of the y-z cross section when the sample was placed at the focal plane of the ultrasonic transducer; and (c) image of the y-z cross section when the sample was placed far from the focal plane of the ultrasonic transducer.
Figure 8:
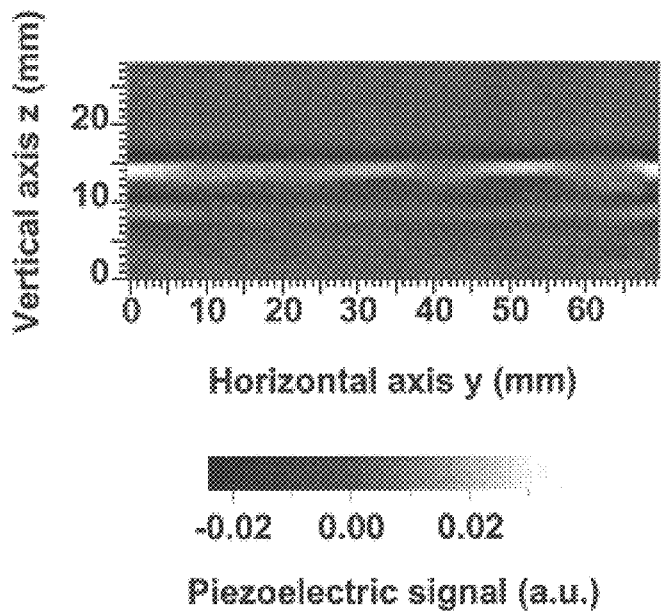
Figure 8:
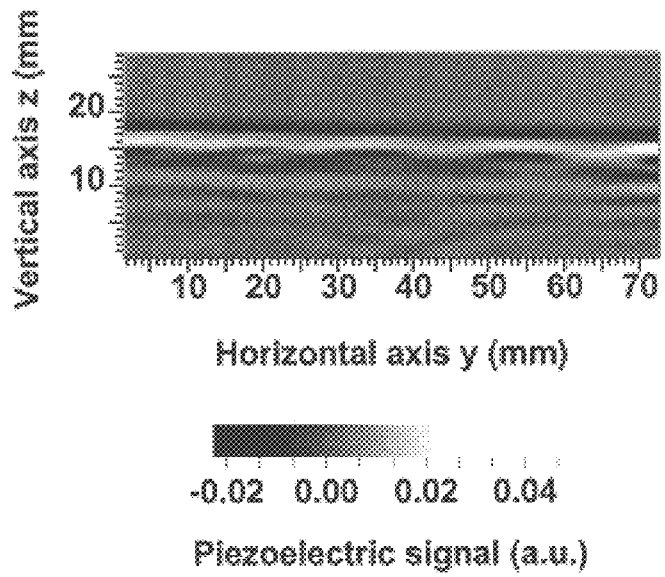

The lateral resolution is determined by the numerical aperture of the ultrasonic transducer. The ultrasonic transducer responds to the thermoacoustic signals along its acoustic axis. The detected source area is related to the numerical aperture of the ultrasonic transducer and the distance between the thermoacoustic source and the ultrasonic transducer. The minimum detected source area is at the focal plane of the ultrasonic transducer. Therefore, a better lateral resolution is expected when the sample is located within the focal column. Examination of the lateral resolution with a 1 MHz ultrasonic transducer is also provided. The ultrasonic transducer has a 3-dB focal diameter of 2.1 mm and a focal zone of 17.6 mm along the acoustic axis. Several pieces of rectangular gel slabs are arranged linearly along the y direction as shown in FIG. 8(a). The y-z cross section is imaged with a step size of 1 mm when the sample is scanned along the y axis. FIG. 8(b) shows the two-dimensional image when the sample is on the focal plane of the ultrasonic transducer. The bright upper band near z=14 mm is the primary image from the thermoacoustic waves propagating directly upward toward the ultrasonic transducer, whereas the dark lower band near z=9 mm is the "ghost" image caused by acoustic reflection from the plastic stand. The gaps of greater than 4 mm can be easily recognized. The gap of 2.5 mm can be barely identified, which defines the lateral resolution and is comparable with the focal diameter of the ultrasonic transducer.

The measured thermoacoustic signal is a convolution between the thermoacoustic signal in the sample and the detection-sensitivity distribution of the ultrasonic transducer over the detected area. The convolution reduces the lateral resolution, which is worsened when the ultrasonic transducer is out of focus. FIG. 8(c) is acquired when the ultrasonic transducer is deliberately moved far away from the sample so as to create defocusing. The gaps are not distinguishable in the 2D image due to reduced resolution.

Figure 9:
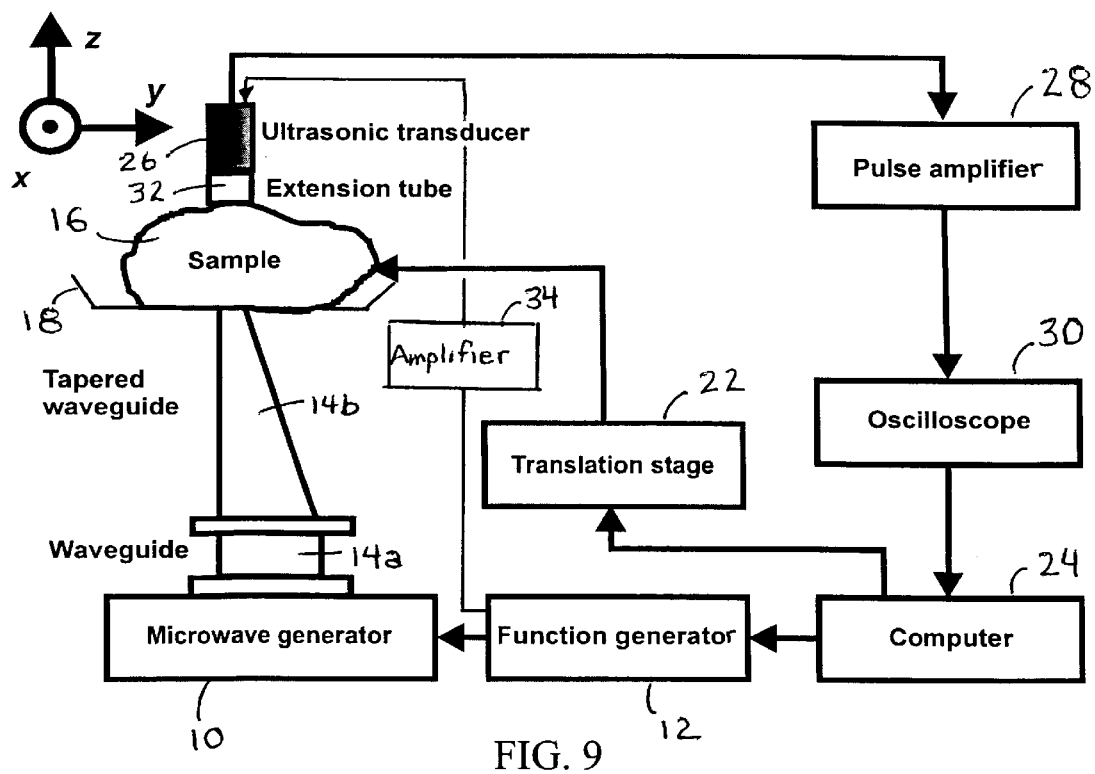
FIG. 9 is a schematic diagram illustrating a scanning thermoacoustic tomography system in accordance with another embodiment of the present invention.
Figure 11:
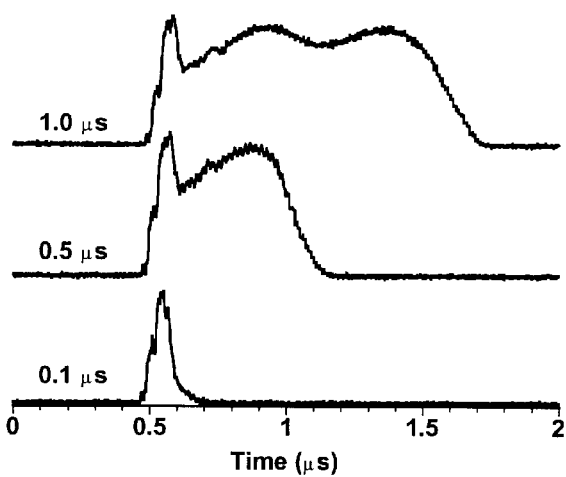
FIGS. 11(a) and 11(b) are graphical illustrations of the effect of microwave-pulse width on the axial resolution of the system.
Figure 11:
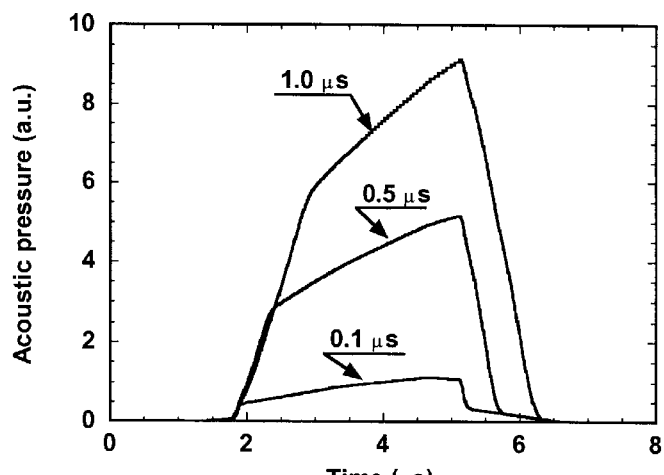
Figure 11:
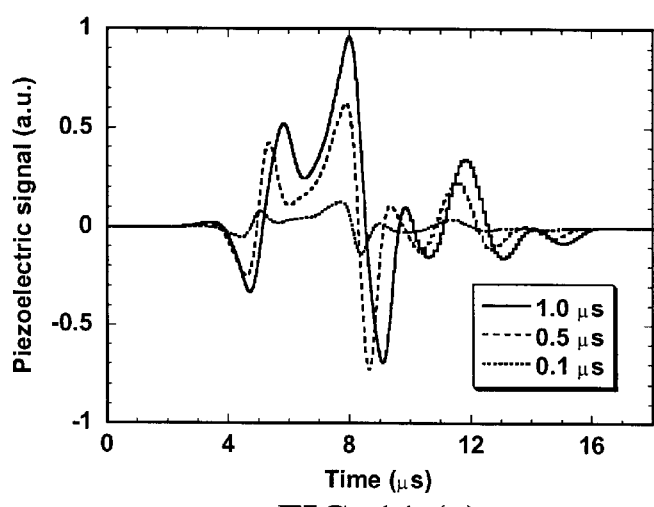

A system for scanning thermoacoustic tomography in accordance with another embodiment of the present invention is shown in FIG. 9. The same Cartesian coordinate system is set up for reference. The z axis is along the ultrasonic axis pointing upward. The x axis is along the long side of the exit of the tapered waveguide (perpendicular to the plane of the drawing). The y axis is along the short side of the exit of the tapered waveguide (in the plane of the drawing). Upon receiving a trigger signal from the computer 24, a microwave generator 10 transmits microwave pulses into biological tissue 16 through a standard waveguide 14a and a tapered waveguide 14b. The tapered waveguide 14b is used to focus the microwave energy into a narrow wave. An ultrasonic transducer 26 receives the thermoacoustic signal emitted from inside the tissue 16. The acoustic axis of the ultrasonic transducer 26 is in the volume of microwave emission determined by the tapered waveguide 14b. A pulse amplifier 28 amplifies the signal from the ultrasonic transducer 26. The amplified signal is digitized and averaged in an oscilloscope 30 and then transferred to the personal computer 24.

In an exemplary embodiment, the microwave generator 10 in FIG. 9 may comprise a 3 GHz generator, with a peak power of approximately 30 kw, a pulse width of 0.5 $\mu$s and an estimated energy of 5 $\mu$J per pulse. A Stanford Research System DS345 function generator 12 may be used to trigger the microwave generator 10, control its pulse repetition frequency, and synchronize the oscilloscope sampling. The standard waveguide 14a may have a cross section of 72 mm×34 mm, and the tapered waveguide 14b may have a cross section of 72 mm×5 mm.

The sample to be imaged is placed on a holder 18, which is supported on a two-dimensional x-y Arrick Robotics MD2 translation stage 22. The holder preferably has an opening (not shown) aligned with the exit (upper) end of the tapered waveguide 14b. The two x-y stepper motors of the translation stage 22 are controlled by the computer 24. An extension tube 32, filled with an acoustic-coupling medium, may be mounted on the acoustic transducer 26. The extension tube 32 is of a length such that its focal zone is inside the region of imaging interest in the sample 16. The bottom surface of the extension tube 32 is configured and arranged to be in contact with the sample 16 for good acoustic coupling. The acoustic transducer may comprise a Panametrics V314 transducer, with a central frequency of 1 MHz, a bandwidth of 0.6 MHz, a diameter of 1.9 cm, a focal length of 2.5 cm, and a focal diameter at 1 MHz of 0.2 cm. The oscilloscope 30 may comprise a Tektronix TDS-640A unit and preferable averages the amplified signal from the pulse amplifier 28 from 10–100 times to enhance signal strength.

The alternatives to the use of a single-element focused transducer described in connection with the embodiment of FIG. 2 are also applicable here.

As previously described, the ultrasonic transducer detects the time-of-arrival signal from the acoustic sources inside the tissue. The distance between the acoustic sources and the ultrasonic transducer is calculated by multiplying the time of arrival and the speed of sound in the tissue. Therefore, a time-domain signal can be converted into a one-dimensional image along the transducer axis (z axis). Scanning the transducer rectilinearly across the sample along the x or y axis yields a two-dimensional cross sectional image of the tissue in the x-z or y-z plane. Furthermore, scanning the transducer across the sample along the x and y axes yields a three-dimensional image of the tissue. During the scanning, the acoustic axis of the ultrasonic transducer must be kept in the volume of microwave emission determined by the tapered waveguide 14b.

The narrow elongated output port of the tapered waveguide may be considered as a "line source" of electromagnetic radiation. Cylindrical wave propagation may be assumed throughout the frequency range in the simulation of the thermoacoustic signal. An electromagnetic wave emitted from the tapered waveguide 14b and attenuated in tissue may be approximated as $$I(z) = I_0 \frac{\exp(-2\alpha z)}{\sqrt{z}}, \tag{10}$$

where $I_0$ is the intensity at the output port of the tapered waveguide, z is the distance from the output port to the point of observation along the vertical axis, I(z) is the intensity at z, and $\alpha$ is the field absorption coefficient in tissue and is expressed in Eq. (2) above.

As previously discussed in connection with FIG. 1, in the frequency range of 0.1–10 GHz, the dielectric constant (ratio of the permittivity in the material to that in vacuum) has a value of 5–70 for soft tissues, and the conductivity has a value of 0.02–3 $\Omega^{-1}$ m$^{-1}$. The complex dielectric properties of tissues at various microwave frequencies determine the propagation and absorption distribution of microwave. Consequently, the induced thermoacoustic pressure depends on the intensity of microwave and the complex dielectric constant of the material.

A simplified model may be used to estimate the microwave-induced thermoacoustic pressure. A small breast tumor was embedded in normal breast tissue. The normal tissue predominantly determined the microwave attenuation. The thermoacoustic pressure p is proportional to the local absorbed microwave power:

$$p \propto I_0 \frac{2\alpha \exp(-2\alpha z)}{\sqrt{z}}. \tag{11}$$

The ultrasonic transducer responds to the thermoacoustic components within its response bandwidth and rejects the components outside the bandwidth. The piezoelectric signal $V_p$ from the ultrasonic transducer is proportional to the thermoacoustic contrast:

$$V_p (p_t - p_n), \tag{12}$$

where $p_t$ and $p_n$ are respectively the thermoacoustic pressures in the tumor and the normal background tissue at depth z where the tumor and the normal tissue interface.

Based on Eqs. (11) and (12), the following expression for $V_p$ is obtained:

$$V_p \propto I_0 \frac{2(\alpha_t - \alpha_n)\exp(-2\alpha_n z)}{\sqrt{z}}, \tag{13}$$

where $\alpha_t$ and $\alpha_n$ represent the microwave-absorption coefficients of the tumor and the normal breast tissue, respectively.

Figure 10:
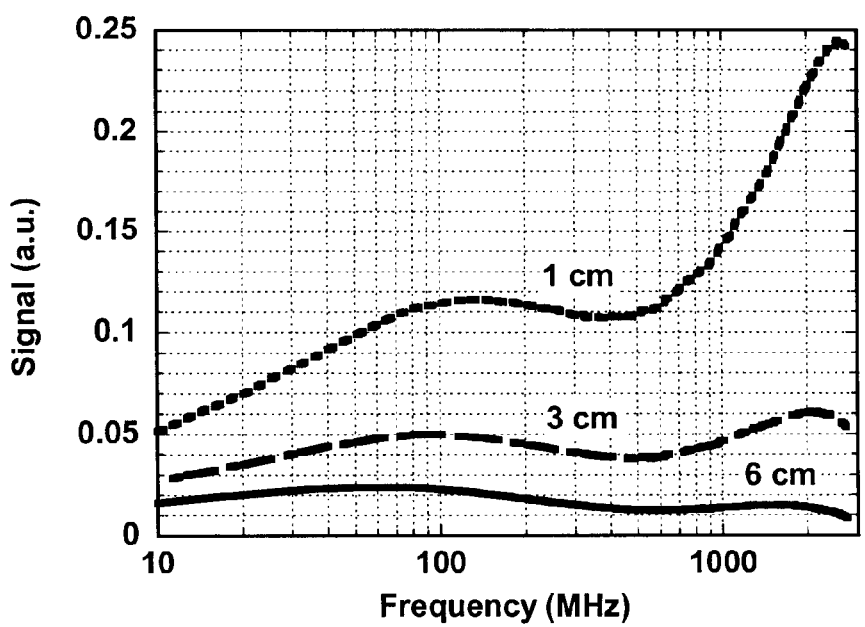
FIG. 10 is a graphical illustration of the thermoacoustic signal strength as a function of the microwave frequency and the tumor depth within a tissue.

Using Eq. (13), the piezoelectric signal was calculated as a function of the microwave frequency and tumor location within the sample. The results are shown in FIG. 10. If the detection system is instrument-noise limited, the signal-to-noise ratio (SNR) of the system is different from this piezoelectric signal by a constant factor. The noise in the detection system of FIG. 9 was mainly from the pulse amplifier 28 used to amplify the piezoelectric signal from the ultrasonic transducer 26. The noise remained almost constant in the experiment and was independent of the microwave frequency or the depth of the tumor. As shown in FIG. 10, the SNR decreases as the tumor depth increases because of the increasingly attenuated microwave intensity. When the tumor is located near the tissue surface, e.g., at 1 cm depth, the SNR is better at higher frequencies. When the tumor is located more deeply, the choice of frequency for an optimal SNR is rather broad. This is because the decrease in thermoacoustic pressure is compensated by the increasing difference of the RF-absorption coefficients between the tumor and normal breast tissues as the frequency increases.

The axial resolution is limited by two factors: the temporal width of the microwave pulse and the temporal width of the impulse response of the ultrasonic transducer. The temporal width of the impulse response of the ultrasonic transducer is inversely proportional to the bandwidth of the ultrasonic transducer. To illustrate the effect of the microwave-pulse width on the axial resolution, the thermoacoustic pressures and the corresponding piezoelectric signals from a microwave-absorbing slab of 5 mm in thickness were simulated using Eq. (11) and the convolution method described previously. The excitation microwave pulses had the same peak power but different pulse widths: 1.0 $\mu$s, 0.5 $\mu$s, and 0.1 $\mu$s. See FIG. 10. There are two dipolar structures corresponding to the two boundaries of the slab. The width of the dipolar structures is determined by the width of the microwave pulses and the impulse response time of the ultrasonic transducer. The distance between the dipolar structures is determined by the acoustic-transit time across the slab. For the 5-mm thick slab, the acoustic-transit time was 3.3 $\mu$s based on the speed of sound of ~1.5 mm/$\mu$s. Pumping with a narrower microwave pulse decreases the width of the dipolar structures and therefore improves the axial resolution because the dipolar structures define the time window for axial resolution. The narrower microwave pulses of the same peak pressure also produce smaller signals. Likewise, an ultrasonic transducer of a higher central frequency and a broader bandwidth produces narrower dipolar structures and therefore improves the axial resolution at the expense of signal strength.

The lateral resolution at the focal plane is limited by the focal diameter of the ultrasonic transducer. Based on the ultrasound reciprocity, the focal determines both the beam diameter when the ultrasonic transducer transmits ultrasound and the detection directivity factor when the ultrasonic transducer detects ultrasound. The focal diameter is approximately determined by $$\phi_f = \lambda_a/NA = c_a/(NA f_a) \tag{14}$$

where $\lambda_a$ represents the acoustic wavelength, NA represents the numerical aperture of the ultrasonic transducer, $c_a$ represents the speed of sound, and $f_a$ represents the central frequency of the piezoelectric signal. The numerical aperture NA is solely determined by the ultrasonic transducer. The speed of sound $c_a$ is relatively constant throughout the frequency range. The central frequency of the piezoelectric signal $f_a$ is determined by the frequency spectrum of the thermoacoustic signal in the dipolar structures and the frequency response of the ultrasonic transducer. Therefore, the lateral resolution is not only related to the ultrasonic parameters including the numerical aperture and the frequency response of the ultrasonic transducer but also related to the frequency content of the thermoacoustic signal in the dipolar structures. A high frequency is obviously desired for high-resolution imaging.

The ultrasonic transducer functions as a frequency filter to the thermoacoustic signals. The homogeneous tissue between interfaces produces slowly varying pressure signals caused by electromagnetic propagation and absorption. The slowly varying signals are outside the bandwidth of the ultrasonic transducer and therefore rejected. The variations in microwave absorption at tissue interfaces cause abrupt changes in thermoacoustic pressure. The abruptly varying signals have frequency components falling into the response bandwidth of the ultrasonic transducer and provide main contribution to the piezoelectric signals of the ultrasonic transducer. An ultrasonic transducer of a higher central frequency would provide better lateral resolution. An ultrasonic transducer of a higher central frequency usually has a broader bandwidth and would consequently yield better axial resolution as well. When the resolution is improved by varying the ultrasonic parameters, the SNR is reduced because the volume of thermoacoustic signal contributing to the piezoelectric signal is reduced. Therefore, there is a trade-off between imaging resolution and SNR.

Biological tissue itself also functions as a frequency filter to the thermoacoustic signals. Higher-frequency components experience greater attenuation than the lower-frequency components. This attenuation is severe for the high-frequency components that pass through a long path in biological tissue. The preferential reduction in the high-frequency components would adversely affect the imaging resolution.

Figure 12:
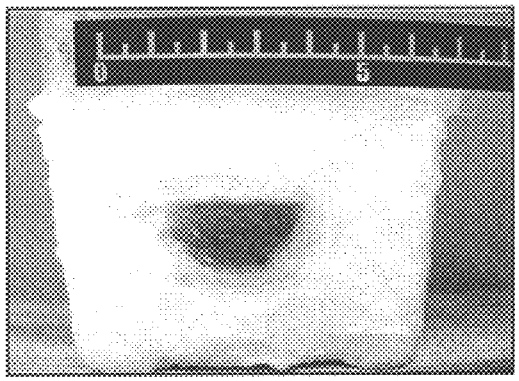
FIG. 12(a) is a cross sectional view of a sample comprised of muscle tissue embedded in lard.
FIG. 12(b) is a two-dimensional thermoacoustic image of the sample as scanned along the y-z axis.
FIG. 12(c) is a graphical illustration of the temporal thermoacoustic signal for y equal to 23 mm.
Figure 12:
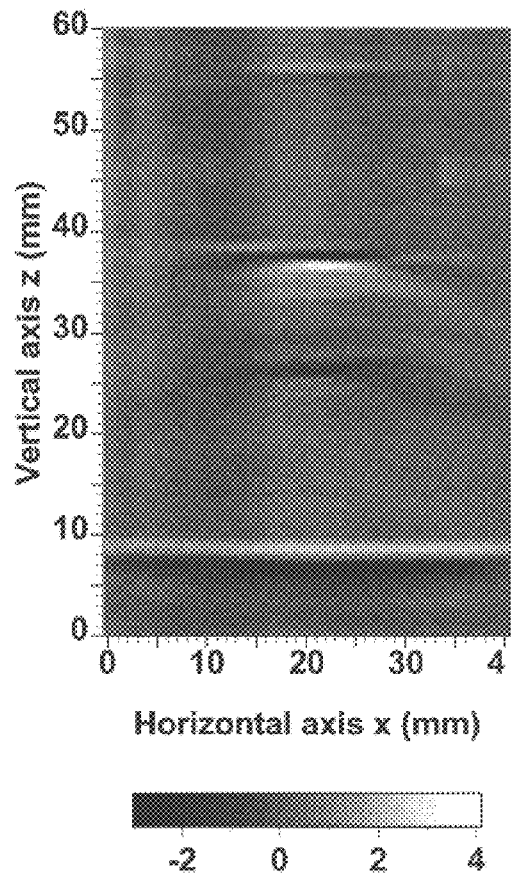
Figure 12:
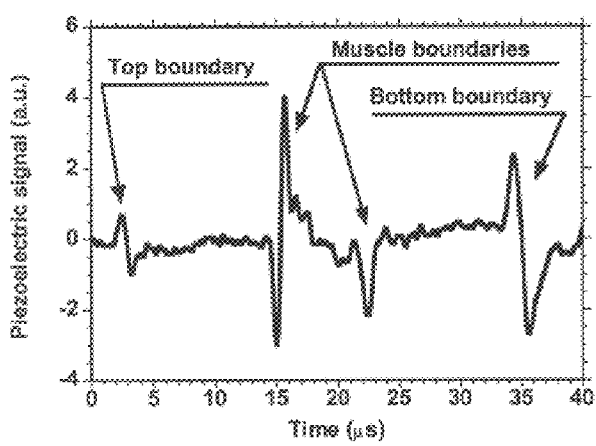

Two samples were scanned with the microwave-induced thermoacoustic imaging system illustrated and described in connection with FIG. 9. These samples are shown in cross section in FIGS. 12(a) and 13(a). The background of the first sample was made intentionally as homogeneous as possible. A piece of muscle tissue was embedded into lard before it solidified, where the lard was used for its homogeneity. As shown in FIG. 12(a), the sample was cut across to reveal the cross section after it was imaged with scanning thermoacoustic tomography. The time-resolved thermoacoustic signals were acquired at each step while the sample was scanned horizontally along they axis with a step size of 1 mm. The resulting two-dimensional image is shown in FIG. 12(b). Each vertical line in this two-dimensional thermoacoustic was obtained from a temporal thermoacoustic waveform. FIG. 12(c) shows the temporal thermoacoustic signal for y equal to 23 mm as an example. The earliest arriving signal came from the upper surface of the lard. The following signals corresponded to the two surfaces of the muscle and the bottom surface of the lard.

Because the sample is in the near field of microwave, a logical question is whether the heterogeneity of the electromagnetic field would cause heterogeneity in thermoacoustic images. As shown in FIG. 12(c), the signal from the background lard is very weak, indicating the heterogeneity of the electromagnetic field does not affect thermoacoustic imaging significantly. The heterogeneity of the electromagnetic field is of the scale of the wavelength. The wavelength is several centimeters in biological tissue at the 3 GHz frequency. Spatial variations of this scale correspond to low-frequency thermoacoustic signals and are therefore filtered out by the ultrasonic transducer.

The background of the second sample was left with some heterogeneity. A piece of swine muscle tissue of ~5 mm in thickness was buried inside a piece of swine fat tissue. The fat tissue was naturally separated into several layers by thin (<1 mm in thickness) connective tissue that has greater microwave absorption than the adjacent fat tissue. FIG. 12(a) shows a cross section of the sample as exposed and photographed after the sample was imaged with the scanning thermoacoustic imaging system to FIG. 9. Both the buried muscle and the connective tissue are clearly visible.

Figure 13:
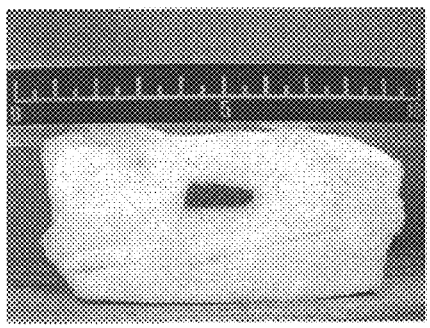
FIG. 13(a) is a cross sectional view of a sample comprised of swine muscle tissue within swine fat tissue.
FIG. 13(b) is a two-dimensional thermoacoustic image of the sample as scanned along the y-z axis.
FIG. 13(c) is a graphical comparison of the original thermoacoustic signal and the gain-compensated thermoacoustic signal at y equal to 20 mm.
FIG. 13(d) is a gain-compensation two-dimensional image of the sample.
Figure 13:
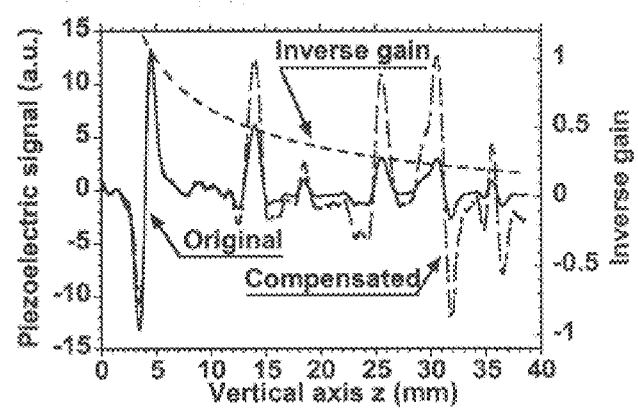
Figure 13:
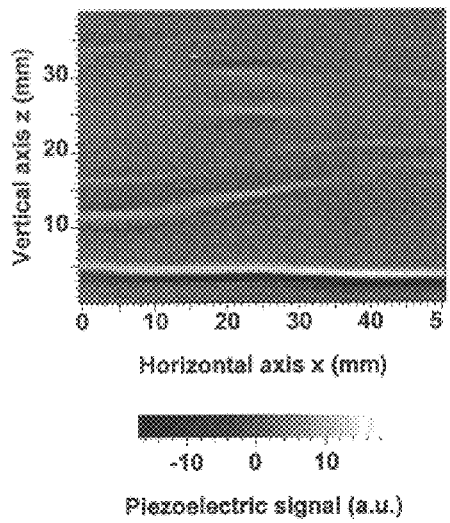
Figure 13:
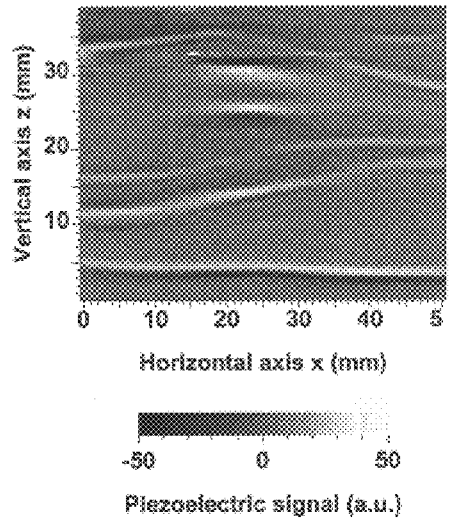

Because of microwave attenuation in tissue, the deeper tissue structures received less microwave radiation and produced weaker thermoacoustic signals. Consequently, the deeper structures were not as clearly imaged as the shallower ones. See FIG. 13(b). To enhance the image contrast, the piezoelectric signal was compensated with the following factor:

$$g(z) = \sqrt{z} \exp(2\alpha z), \tag{15}$$

which is the inverse of microwave intensity attenuation. In FIG. 13(c), the original piezoelectric signal for y equal to 20 mm was plotted with a solid line. The microwave-induced thermoacoustic signal decreased for increasing distance z. The inverse of the compensated gain was added into the FIG. 13(c) with a dashed line for a comparison with the decay of the original piezoelectric signal. The deeper signal would be compensated with a greater gain. The compensated data, plotted with a point-dashed line, had nearly constant amplitude throughout the imaged depth. The gain-compensated image, shown in FIG. 13(d), shows the deeper structures clearly as well. Some interference from the pulse amplifier was also amplified by the "gain compensation" and shown as the artifacts in the image near the upper surface of the muscle tissue. This technique is similar to the "time-gain compensation" in conventional ultrasonography.

Alternatively, the system illustrated in FIG. 9 may be used to obtain traditional ultrasonograms of the same sampling volume as the thermoacoustic tomography has covered. At each position of the ultrasonic transducer, a one-dimensional thermoacoustic image and a one-dimensional ultrasonographic image may be obtained sequentially. Both images measure the same line defined by the ultrasonic axis. Scanning the ultrasonic transducer can generate two-dimensional or three-dimensional images of both the types for co-registration in real time.

In the generation of ultrasonograms, an electric pulse is produced by the pulse generator 12 upon receiving a trigger signal from the computer 24. The pulse is amplified by an amplifier 34 and then applied to the ultrasonic transducer 26. An acoustic pulse is emitted into the tissue along the acoustic axis. When the acoustic wave encounters mismatches of acoustic impedance, acoustic echoes can be detected by the ultrasonic transducer 26. The time of arrival can be converted to distance along the acoustic axis by dividing it by the speed of sound and by two because of the round-trip delay. Therefore, the time-domain echo signal can be converted into a one-dimensional image along the acoustic axis. Ultrasonography is a well established technique and, therefore, is not further detailed here.

Figure 14:
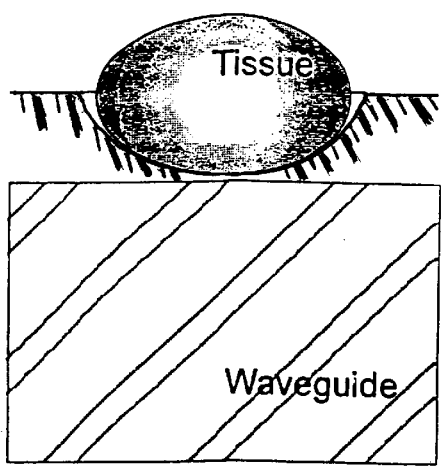
FIGS. 14(a) and 14(b) are schematic views illustrating two techniques for focusing the electromagnetic beam within the region of interest in the tissue to be imaged.
Figure 14:
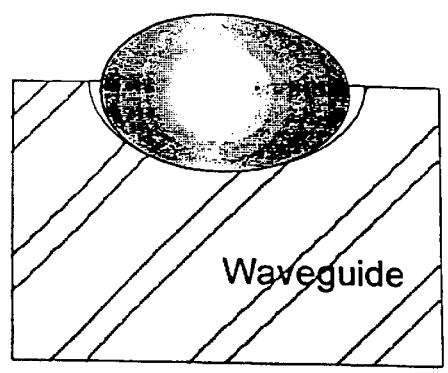

Because of the attenuation and diffraction of electromagnetic wave in biological tissues, the energy deposition near the surface of the tissues is greater than that inside the tissues. Energy deposition inside the tissues may be increased by focusing the electromagnetic wave. There are two potential schemes for focusing. The first approach is to bend the tissue surface as shown in FIG. 14(a). The second approach is to curve the exit and of the waveguide and to bend the tissue surface accordingly as shown in FIG. 14(b). A microwave-transparent cover may be placed over the end of the waveguide to ensure good energy coupling to the tissue and to protect the tissue against injury.

Although, as described, the present invention affords particular advantages in image scanning where the thermoacoustic-inducing radiation is in the microwave range, other energy ranges, such as the optical range, may also be similarly used. In such case, the microwave generator 10 would be replaced by a laser.

Although the invention has been described herein by reference to specific embodiments thereof, it will be understood by those skilled in the art that such embodiments are susceptible of variation and modification without departing from the inventive concepts disclosed. All such variations and modifications, therefore, are intended to be encompassed within the spirit and scope of the appended claims.

What is claimed is:

1. A method of electromagnetically-induced thermoacoustic imaging of biological tissue, comprising:
   (a) repetitively irradiating the tissue to be imaged with short pulses of electromagnetic energy to induce thermoacoustic waves within the tissue, including the step of compressing the electromagnetic energy to a narrow wave in the region of irradiation of the tissue wherein the frequency of the electromagnetic energy is within the range of from 300 MHz to 3 GHz and the duration of the electromagnetic pulses is within the range of from 0.1 µs to 0.5 µs;
   (b) detecting the thermoacoustic waves with at least one focused ultrasonic transducer and generating time-domain signals in response thereto; and
   (c) converting the time-domain signals to a one-dimensional image of the tissue along the acoustic axis of the transducer.

2. The method of claim 1, further comprising:
   (d) scanning the tissue in a first direction transverse to the acoustic axis of the transducer and repeating steps (a), (b) and (c) at each of a plurality of spaced points along said first direction to provide a two-dimensional image of the tissue.

3. The method of claim 2, further comprising:
   (e) scanning the tissue in a second direction transverse to the acoustic axis of the transducer and transverse to the first direction and repeating steps (a), (b) and (c) at a plurality of spaced points along said second direction to provide a three dimensional image of the tissue.

4. The method of claim 1, wherein the acoustic axis of the ultrasonic transducer of step (b) is located within the volume of the electromagnetic energy.

5. The method of claim 4, wherein said at least one transducer is a focused single-element transducer.

6. The method of claim 1, wherein the electromagnetic energy constitutes a line source of electromagnetic radiation.

7. The method of claim 1, wherein the electromagnetic energy is compressed by use of a tapered wave guide.

8. The method of claim 1, wherein step (c) further comprises gain compensating the one-dimensional image for microwave intensity attenuation within the tissue.

9. The method of claim 8, wherein said gain compensation is a function of the inverse of microwave intensity attenuation within the tissue.

10. The method of claim 1, wherein steps (a)–(c) are carried out in real time.

11. The method of claim 1, further comprising:
   (d) interrupting steps (a)–(c);
   (e) repetitively energizing the transducer to emit acoustic pulses into the tissue to be imaged;
   (f) detecting acoustic echoes from the tissue with the transducer and generating time-domain echo signals in response thereto; and
   (g) converting the time-domain echo signals into a one-dimensional image along the acoustic axis of the transducer.

12. The method of claim 11, wherein steps (a)–(g) are carried out in real time.

13. The method of claim 1, wherein step (a) further comprises focusing the electromagnetic energy on the zone of the tissue to be imaged.

14. The method of claim 13, wherein said focusing is accomplished by providing a curved illumination interface at the surface of the tissue to be imaged.

15. An apparatus for electromagnetically-induced thermoacoustic imaging of biological tissue, comprising:
   (a) a source for repetitively irradiating the tissue to be imaged with short pulses of electromagnetic energy to induce thermoacoustic waves within the tissue, the electromagnetic energy source including structure for compressing the electromagnetic energy to a narrow wave in the region of irradiation of the tissue wherein the frequency of the electromagnetic energy is within the range of from 300 MHz to 3 GHz and the duration of the electromagnetic pulses is within the range of from 0.1 µs to 0.5 µs;
   (b) at least one focused ultrasonic transducer for detecting the thermoacoustic waves and generating time-domain signals in response thereto; and
   (c) a computational device for converting the time-domain signals to a one-dimensional image of the tissue along the acoustic axis of the transducer.

16. The apparatus of claim 15, further comprising:
   (d) apparatus for scanning the tissue in a first direction transverse to the acoustic axis of the transducer to a plurality of spaced points along said first direction, said irradiating, detecting and signal-converting operations being carried out at each of said spaced points to provide a two-dimensional image of the tissue.

17. The method of claim 16, wherein said scanning apparatus further comprises apparatus for scanning the tissue in a second direction transverse to the acoustic axis of the transducer and transverse to the first direction to a plurality of spaced points along said second direction, said irradiating, detecting and signal-converting operations being carried out at each of said spaced points in said second direction to provide a three-dimensional image of the tissue.

18. The apparatus of claim 15, wherein the acoustic axis of the ultrasonic transducer is located within the volume of the electromagnetic energy.

19. The apparatus of claim 18, wherein said at least one transducer is a focused single-element transducer.

20. The apparatus of claim 15, wherein the electromagnetic wave constitutes a line source of electromagnetic radiation.

21. The apparatus of claim 15, wherein the electromagnetic energy is compressed by use of a tapered waveguide.

22. The apparatus of claim 15, further comprising means for gain compensating the one-dimensional image for microwave intensity attenuation within the tissue.

23. The apparatus of claim 22, wherein said gain compensation is a function of the inverse of microwave intensity attenuation within the tissue.

24. The apparatus of claim 15, wherein the irradiating, detecting and signal converting operations of paragraphs (a)–(c) are carried out in real time.

25. The apparatus of claim 15, further comprising:
  (d) control circuitry for repetitively energizing the transducer to emit acoustic pulses into the tissue to be imaged;
  (e) said transducer being operable to detect acoustic echoes from the tissue with the transducer and generate time-domain echo signals in response thereto; and
  (f) said computational device being operable to convert the time-domain echo signals into a one-dimensional image along the acoustic axis of the transducer.

26. The apparatus of claim 25, wherein the operations of paragraphs (a)–(f) are carried out in real time.

27. The apparatus of claim 15, further comprising a curved illumination interface at the surface of the tissue to be imaged.

28. A method of electromagnetically-induced thermoacoustic imaging of biological tissue, comprising:
  (a) repetitively irradiating the tissue to be imaged with short pulses of electromagnetic energy to induce thermoacoustic waves within the tissue, including the step of compressing the electromagnetic energy to a narrow wave in the region of irradiation of the tissue;
  (b) detecting the thermoacoustic waves with an array of unfocused ultrasonic transducer elements and generating time-domain signals in response thereto; and
  (c) synthetically focusing the time-domain signals to generate a tomographic image of the tissue.

29. The method of claim 28, wherein the electromagnetic energy constitutes a line source of electromagnetic radiation.

30. The method of claim 28, wherein the electromagnetic energy is compressed by use of a tapered wave guide.

31. The method of claim 28, wherein the frequency of the electromagnetic energy is within the range of from 300 MHz to 3 GHz and the duration of the electromagnetic pulses is within the range of from 0.1 $\mu$s to 0.5 $\mu$s.

32. The method of claim 28, wherein step (c) further comprises gain compensating the image for microwave intensity attenuation within the tissue.

33. The method of claim 32, wherein said gain compensation is a function of the inverse of microwave intensity attenuation within the tissue.

34. The method of claim 28, wherein steps (a)–(c) are carried out in real time.

35. The method of claim 28, further comprising:
  (d) interrupting steps (a)–(c);
  (e) repetitively energizing at least one transducer element to emit acoustic pulses into the tissue to be imaged;
  (f) detecting acoustic echoes from the tissue with at least one transducer element and generating time-domain echo signals in response thereto; and
  (g) generating an ultrasonographic image from the time-domain echo signals.

36. The method of claim 35, wherein steps (a)–(g) are carried out in real time.

37. The method of claim 28, wherein step (a) further comprises focusing the electromagnetic energy on the zone of the tissue to be imaged.

38. The method of claim 37, wherein said focusing is accomplished by providing a curved illumination interface at the surface of the tissue to be imaged.

39. An apparatus for electromagnetically-induced thermoacoustic imaging of biological tissue, comprising:
  (a) a source for repetitively irradiating the tissue to be imaged with short pulses of electromagnetic energy to induce thermoacoustic waves within the tissues, the electromagnetic energy source including structure for compressing the electromagnetic energy to a narrow wave in the region of irradiation of the tissue;
  (b) an array of unfocused ultrasonic transducer elements for detecting the thermoacoustic waves and generating time-domain signals in response thereto; and
  (c) a computational device for synthetically focusing the time-domain signals to generate a tomographic image of the tissue.

40. The apparatus of claim 39, wherein the electromagnetic energy constitutes a line source of electromagnetic radiation.

41. The apparatus of claim 39, wherein the electromagnetic energy is compressed by use of a tapered waveguide.

42. The apparatus of claim 39, wherein the frequency of the electromagnetic energy is within the range of from 300 MHz to 3 GHz and the duration of the electromagnetic pulses is within the range of from 0.1 $\mu$s to 0.5 $\mu$s.

43. The apparatus of claim 39, further comprising means for gain compensating the image for microwave intensity attenuation within the tissue.

44. The apparatus of claim 43, wherein said gain compensation is a function of the inverse of microwave intensity attenuation within the tissue.

45. The apparatus of claim 39, wherein the irradiating, detecting and signal converting operations of paragraphs (a)–(c) are carried out in real time.

46. The apparatus of claim 39, further comprising:
  (d) control circuitry for repetitively energizing at least one transducer element to emit acoustic pulses into the tissue to be imaged;
  (e) at least one transducer element being operable to detect acoustic echoes from the tissue with the transducer and generate time-domain echo signals in response thereto; and (f) said computational device being operable to generate an ultrasonographic image from the time-domain echo signals.

47. The apparatus of claim 46, wherein the operations of paragraphs (a)–(f) are carried out in real time.

48. The apparatus of claim 39, further comprising a curved illumination interface at the surface of the tissue to be imaged.

* * * * *